(12) United States Patent
Graham et al.

(10) Patent No.: US 8,262,036 B2
(45) Date of Patent: Sep. 11, 2012

(54) TRANSFERABLE PATIENT CARE EQUIPMENT SUPPORT

(75) Inventors: Mark A. Graham, Springboro, OH (US); Steven J. Schwartz, Oxford, OH (US)

(73) Assignee: Hill-Rom Services, Inc., Batesville, IN (US)

( * ) Notice: Subject to any disclaimer, the term of this patent is extended or adjusted under 35 U.S.C. 154(b) by 1668 days.

(21) Appl. No.: 11/102,398

(22) Filed: Apr. 8, 2005

(65) Prior Publication Data

US 2006/0043244 A1   Mar. 2, 2006

Related U.S. Application Data

(60) Provisional application No. 60/562,379, filed on Apr. 15, 2004.

(51) Int. Cl.
*F16M 11/00* (2006.01)
(52) U.S. Cl. ............... 248/161; 248/125.8; 248/411; 248/159; 248/157
(58) Field of Classification Search ............ 248/161, 248/688, 122.1, 125.1, 125.2, 125.8, 145.6, 248/407, 409, 411, 159, 157, 176.3
See application file for complete search history.

(56) References Cited

U.S. PATENT DOCUMENTS

| | | |
|---|---|---|
| 1,290,809 A | 1/1919 | Truax |
| 2,470,524 A | 5/1949 | Scudder |
| 2,673,771 A | 3/1954 | Krewson |
| 2,696,963 A | 12/1954 | Shepherd |
| 3,112,910 A * | 12/1963 | Bal ........................... 248/161 |
| 4,113,222 A | 9/1978 | Frinzel |
| 4,185,936 A * | 1/1980 | Takahashi ................ 403/104 |
| 4,262,872 A | 4/1981 | Kodet |
| 4,352,991 A | 10/1982 | Kaufman |
| 4,706,916 A * | 11/1987 | Cullmann et al. ........ 248/168 |
| 4,795,122 A | 1/1989 | Petre |
| 4,905,944 A | 3/1990 | Jost et al. |
| 4,925,444 A | 5/1990 | Orkin et al. |
| 4,945,592 A | 8/1990 | Sims et al. |
| 5,078,349 A | 1/1992 | Smith |
| 5,094,418 A | 3/1992 | McBarnes, Jr. et al. |
| 5,112,019 A | 5/1992 | Metzler et al. |
| 5,117,521 A | 6/1992 | Foster et al. |
| 5,125,607 A | 6/1992 | Pryor |
| 5,135,191 A | 8/1992 | Schmuhl |
| 5,400,995 A | 3/1995 | Boyd |
| 5,407,163 A | 4/1995 | Kramer et al. |
| 5,527,289 A | 6/1996 | Foster et al. |
| 5,593,239 A * | 1/1997 | Sallee ..................... 403/109.3 |
| 5,636,823 A | 6/1997 | Boyd |
| 5,647,491 A | 7/1997 | Foster et al. |
| 5,699,988 A | 12/1997 | Boettger et al. |
| 6,073,285 A | 6/2000 | Ambach et al. |
| 6,082,680 A * | 7/2000 | Woodward et al. ........ 248/682 |
| 6,431,505 B2 | 8/2002 | Chinn et al. |

(Continued)

*Primary Examiner* — Bradley Duckworth
(74) *Attorney, Agent, or Firm* — Kenneth C. Baran (57) ABSTRACT

An equipment support, such as an IV pole, comprises an upper portion, a lower portion having a lower end configured to engage a socket, and an actuator movable relative to the lower end. When the upper portion is gripped by a releasable gripper, the lower end can be disengaged from the socket by moving the actuator from a first position to a second position. The lower portion can be telescoped relative to the upper portion by moving the actuator from the second position to a third position.

19 Claims, 10 Drawing Sheets

U.S. PATENT DOCUMENTS

| | | |
|---|---|---|
| 6,585,206 B2 | 7/2003 | Metz et al. |
| 6,601,860 B2 | 8/2003 | Potter |
| 6,609,686 B2 * | 8/2003 | Malizia ................ 248/125.8 |
| 6,698,698 B1 * | 3/2004 | Hsieh ................... 248/125.8 |
| 6,704,956 B2 | 3/2004 | Riley et al. |
| 6,719,257 B1 * | 4/2004 | Greene et al. .............. 248/411 |
| 2004/0051010 A1 * | 3/2004 | Blackburn ................ 248/163.1 |
| 2004/0108423 A1 * | 6/2004 | Boaro et al. ................ 248/161 |
| 2006/0186284 A1 * | 8/2006 | Root ........................ 248/161 |
| 2006/0242763 A1 | 11/2006 | Graham |

* cited by examiner

TRANSFERABLE PATIENT CARE EQUIPMENT SUPPORT

CROSS-REFERENCE TO RELATED APPLICATIONS

This application claims priority to U.S. Provisional Patent Application Ser. No. 60/562,379 filed Apr. 15, 2004 and entitled "IV Pole Load Release Device," which is incorporated herein by reference.

BACKGROUND OF THE INVENTION

The present disclosure relates to a patient care equipment support, such as an IV pole or IV rack. More particularly, the present disclosure relates to a patient care equipment support that is transferable between a first device, such as a hospital bed, and a second device, such as a support arm or a column.

Hospitalized patients often require patient care equipment to be in close proximity during hospital care. Such patient care equipment is typically supported on a patient care equipment support or rack. Illustratively, the patient care equipment includes any one or more of the following: infusion management equipment, heart monitoring equipment, medical gas delivery equipment, defibrillators, and the like, many of which directly connect to the patient via lines or tubes.

Some equipment supports carrying the patient care equipment are transferable between a patient support apparatus, such as a hospital bed, a stretcher, an ambulatory care chair, and the like, and another support structure, such as a ceiling, floor or wall-mounted service column, an equipment support arm, a floor-supported stand, a wheeled cart, a headwall, a wall of a hospital room, and the like. Such transferable equipment support is disclosed in PCT Pat. App. Ser. No. PCT/US2004/033647 filed Oct. 12, 2004 and entitled "Patient Care Equipment Support Lock," which is hereby incorporated herein by reference.

SUMMARY OF THE INVENTION

The present invention comprises a system that has one or more of the following features or combinations thereof, which alone or in any combination may comprise patentable subject matter:

An equipment support, such as an IV pole or IV rack, comprises an upper portion, a lower portion having a lower end configured to engage a socket, and an actuator movable relative to the lower end. The lower end of the lower portion of the equipment support is configured to engage a socket of a patient support, such as a hospital bed, so that the equipment support extends upwardly from the socket.

When the upper portion is gripped by a releasable gripper, the lower end may be disengaged from the socket by moving the actuator from a first position to a second position. The lower portion may be telescoped relative to the upper portion by moving the actuator from the second position to a third position.

The lower end of the lower portion of the equipment support is telescopically movable relative to the lower portion when the actuator is actuated. In this fashion, when the upper portion of the equipment support is held, for example, by a releasable gripper of an equipment support column, the lower end of the lower portion may be moved upwardly out of engagement with the socket in which it is resting. Thus, the equipment support is provided for use with equipment having a releasable gripper for engaging and supporting the upper portion of the equipment support such that, when the upper portion is so gripped and held, the lower portion can be telescoped relative to the upper portion by actuating the actuator.

The lower portion of the equipment support telescopes relative to the upper portion of the equipment support and, when desired, the lower end of the lower portion will telescope relative to the lower portion itself. The actuator may illustratively be movable between a first position, a second position and a third position relative to the lower portion. Such actuator may be movable to the first position to block the lower portion from telescoping relative to the upper portion and block the lower end from telescoping relative to the lower portion. Such actuator may be movable to the second position to continue to block the lower portion from telescoping relative to the upper portion but allow the lower end to telescope relative to the lower portion. Such actuator may be movable to the third position to allow the lower portion to telescope relative to the upper portion and allow the lower end to telescope relative to the lower portion.

The actuator is configured to provide, in its various selected positions, for movement of the lower portion of the equipment support relative to the upper portion of the equipment support and also for movement of the lower end of the lower portion relative to the lower portion. Illustratively, the actuator, in its selected positions, cooperates with ball locks to hold and to release portions of the equipment support.

Additional features, which alone or in combination with any other feature(s), such as those listed above, may comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures, in which.

DETAILED DESCRIPTION OF THE DRAWINGS

Figure 12:
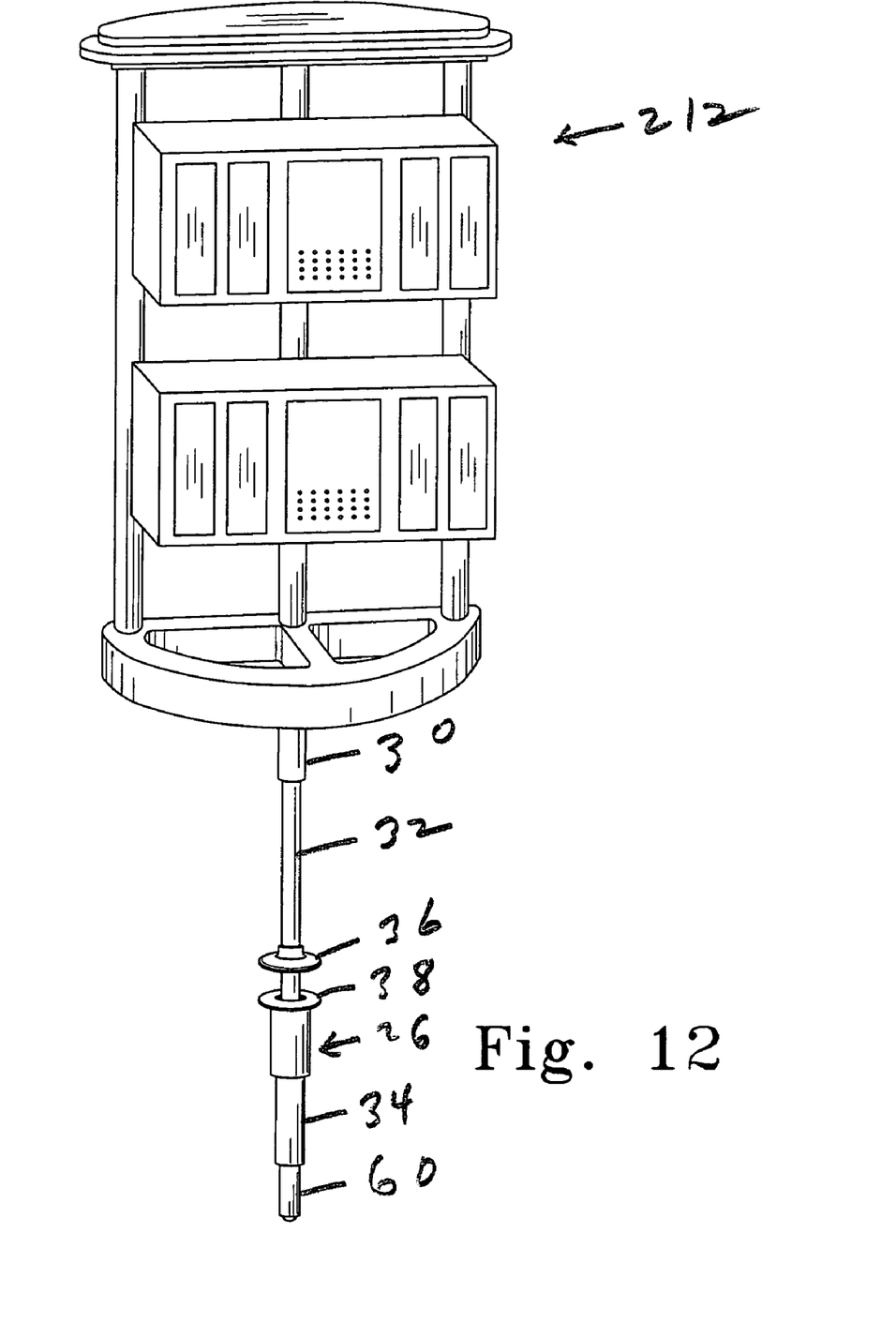
FIG. 12 is a perspective view similar to FIG. 2 of an equipment support carrying patient care equipment, such as infusion pumps.

The present disclosure relates to a patient care equipment support ("equipment support") that is transferable between a first device, such as a hospital bed, and a second device, such as a support arm or a column. Although the equipment support shown in FIGS. 1-8 is a telescoping IV pole 12 for carrying IV bags, the equipment support may very well be an equipment rack, such as the rack 212 shown in FIG. 12, for supporting other types of patient care equipment, such as, for example, infusion pumps. Other equipment supports may include cabinets, shelving units, platforms, accessory rails, and the like.

Figure 1:
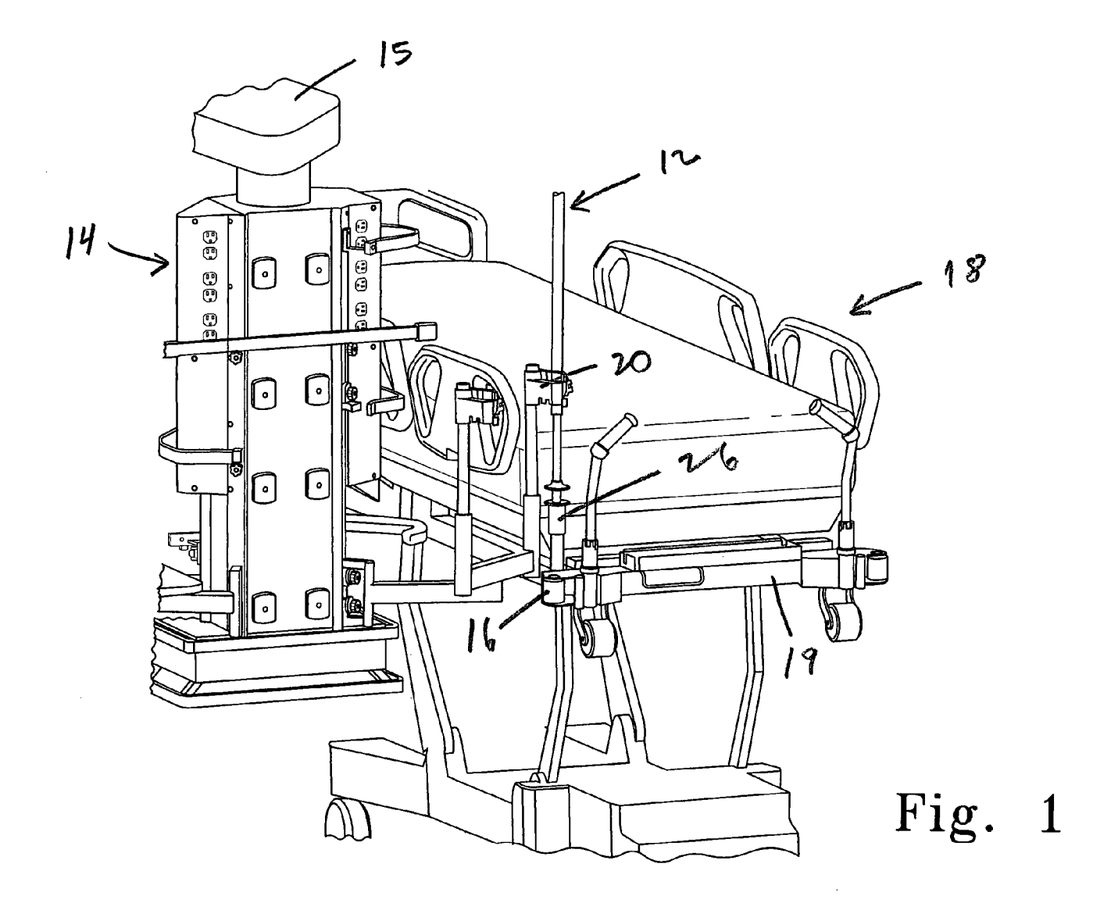
FIG. 1 is a perspective view of a telescoping IV pole adjacent a hospital bed and attached to an equipment support column, and showing the IV pole positioned above a socket carried by the bed.

The IV pole 12 is transferable between a hospital bed 18 and an equipment support column 14 in the embodiment illustrated in FIG. 1. The bed 18 has an upper frame 19 carrying a socket 16 for supporting the IV pole 12. The column 14, carried by a radial support arm 15, has a gripper 20 to releasably grip the IV pole 12 so that the IV pole can be supported by the column 14. Although the IV pole 12 is transferable between the bed 18 and the column 14 in the illustrated embodiment, it should be understood that the IV pole 12 may very well be transferable between other patient supports, such as stretchers, operating tables, ambulatory care chairs, and the like and other equipment supports, such as arms, columns, stands, carts, headwalls, and the like. Also, although the bed 18 has a socket for supporting the IV pole 12, the bed 18 may very well include other means, such as a clamp, for supporting the IV pole 12.

Figure 2:
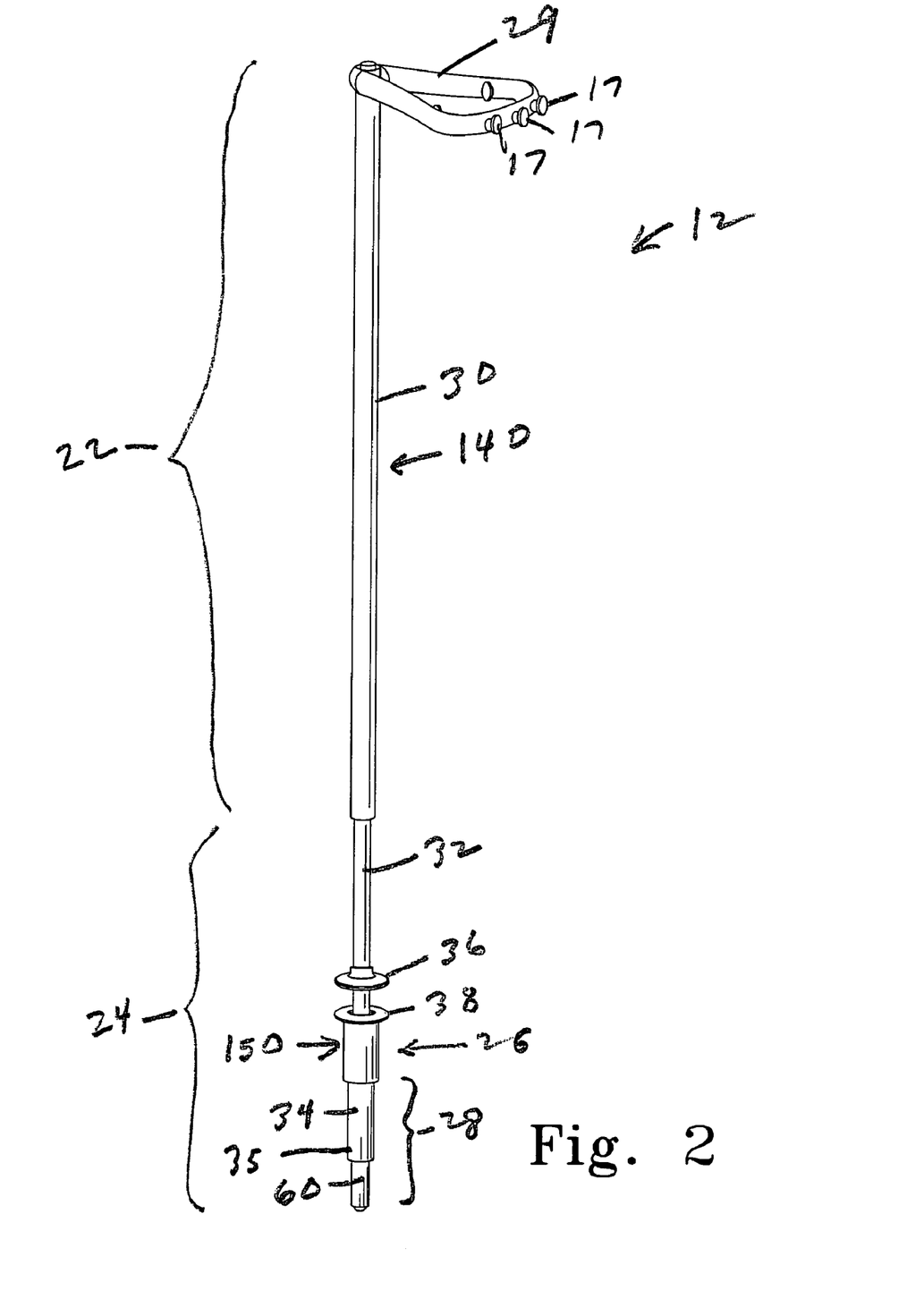
FIG. 2 is a perspective view of the IV pole showing an upper portion, a lower portion having a lower end and an actuator movable relative to the lower end.

As shown in FIG. 2, the IV pole 12 has an upper portion 22 and a lower portion 24. A portion of the upper portion 22 sleeves over a portion of the lower portion 24 for longitudinal telescoping movement relative thereto between a partially extended position shown in FIG. 7 and a partially retracted position shown in FIG. 8. An actuator or a release handle 26 (also referred to as the "slider") is movably coupled to a lower end 28 of the lower portion 24 of the IV pole 12. The actuator 26 is movable between a first or lower position shown in FIG. 3, a second or middle position shown in FIG. 4 and a third or upper position shown in FIG. 5.

Illustratively, the IV pole 12 includes a first or upper tube 30, a second or middle tube 32 and a third or lower tube 34. The upper tube 30 extends substantially the length of the upper portion 22 of the IV pole 12. The middle and lower tubes 32, 34 together extend substantially the length of the lower portion 24 of the IV pole 12. The lower tube 34 including a downwardly-extending post 60 extends substantially the length of the lower end 28 of the lower portion 24 of the IV pole 12. An upper end 31 of the middle tube 32 is housed inside the interior region of the upper tube 30 for longitudinal telescoping movement relative thereto between the partially extended position shown in FIG. 7 and the partially retracted position shown in FIG. 8. In the partially extended position shown in FIG. 7, the middle tube 32 is inserted a first distance 21. In the partially retracted position shown in FIG. 8, the middle tube 32 is inserted a second distance 23 that is larger than the first distance 21. A lower end 33 of the middle tube 32 is housed inside the interior region of the lower tube 34 for longitudinal telescoping movement relative thereto between a partially extended position shown in FIG. 3 and a partially retracted position shown in FIG. 4. A pair of vertically-spaced bushings 52 and 64, coupled to the middle tube 32, are interposed between an inner surface of the lower tube 34 and an outer surface of the middle tube 32. The actuator 26 sleeves over portions of the middle and lower tubes 32, 34.

Figure 3:
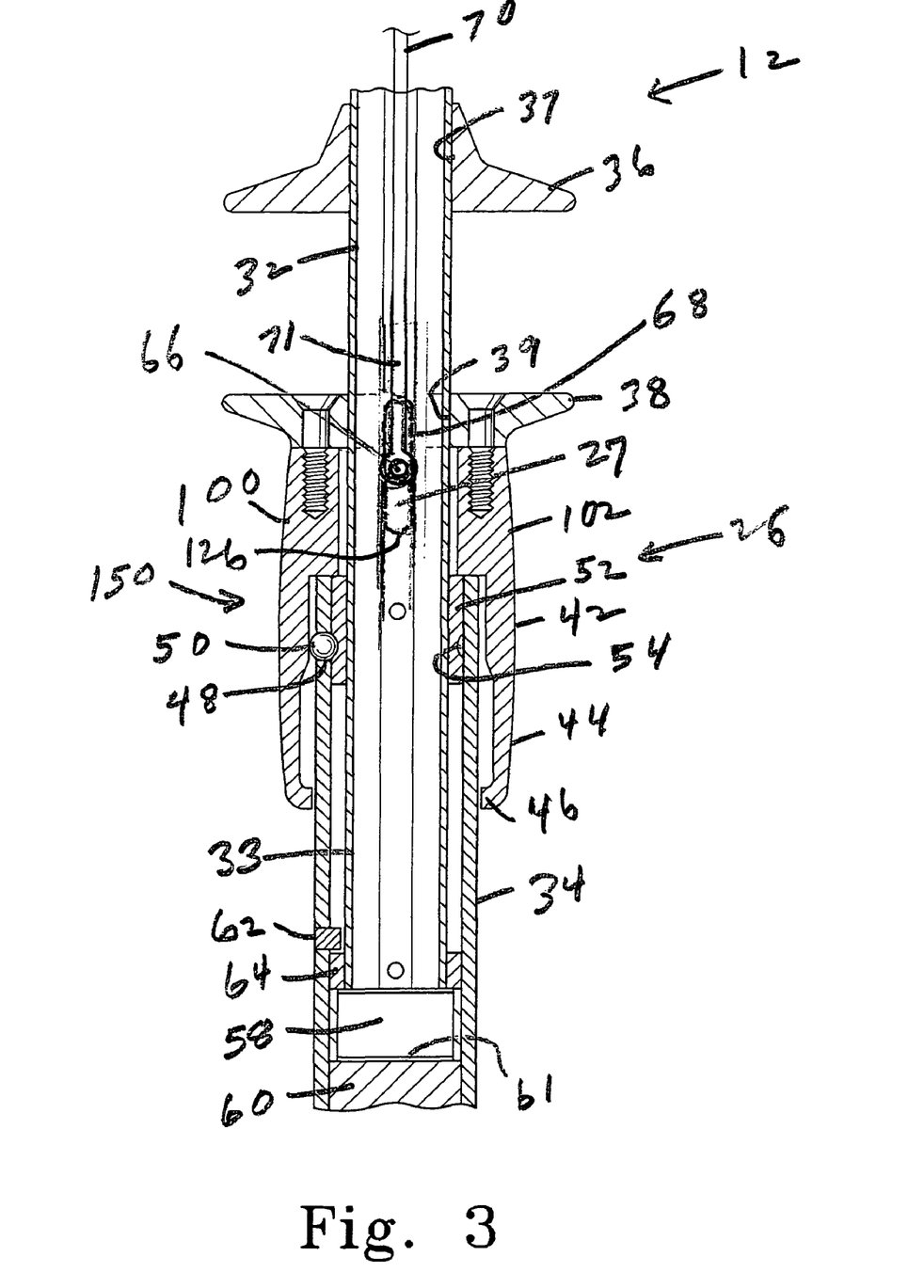
FIG. 3 is a cross-sectional view of the lower portion of the IV pole showing a lower lock cooperating with the actuator in a first or lower position.
Figure 4:
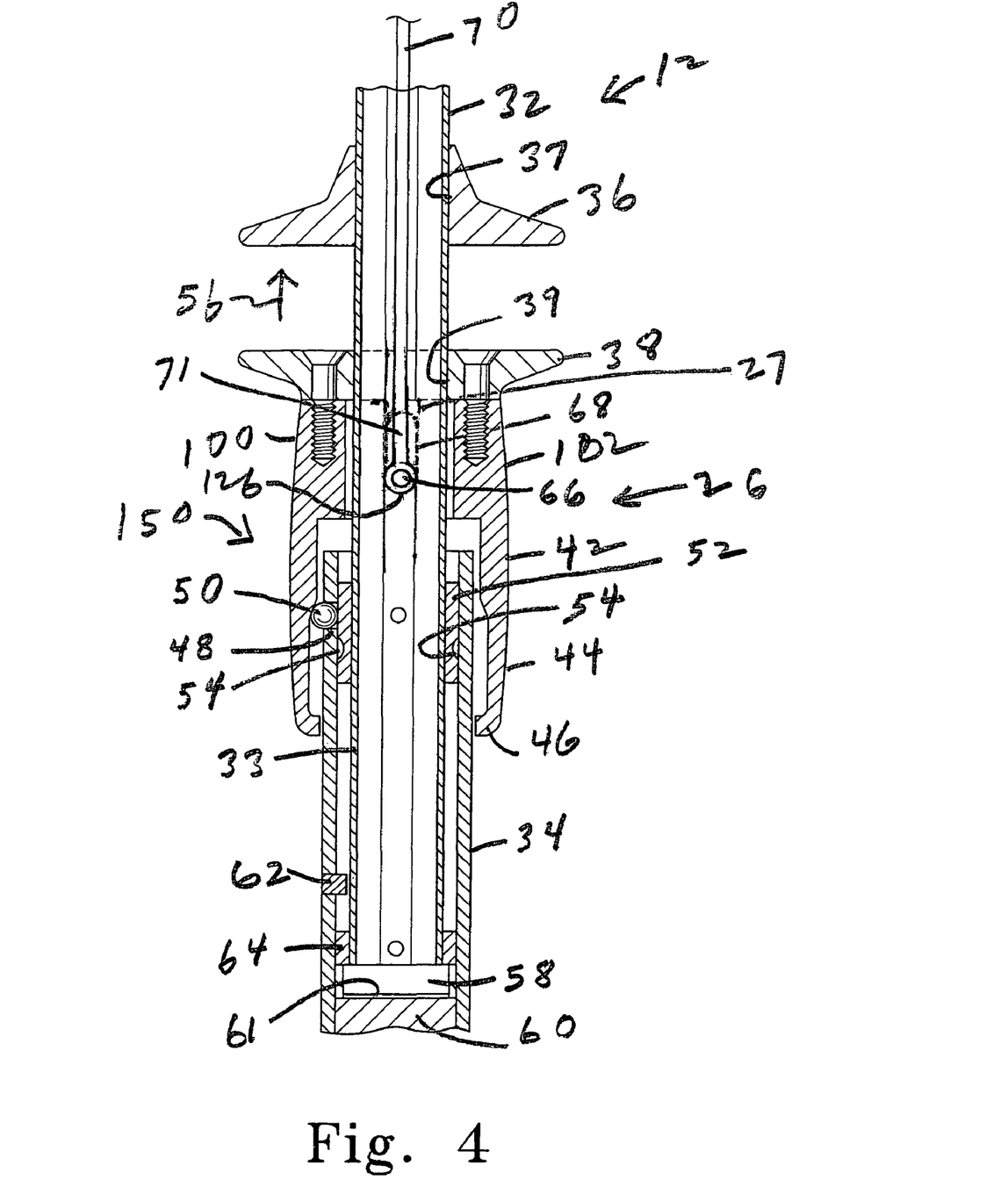
FIG. 4 is a cross-sectional view similar to FIG. 3 showing the actuator in a second or middle position.
Figure 5:
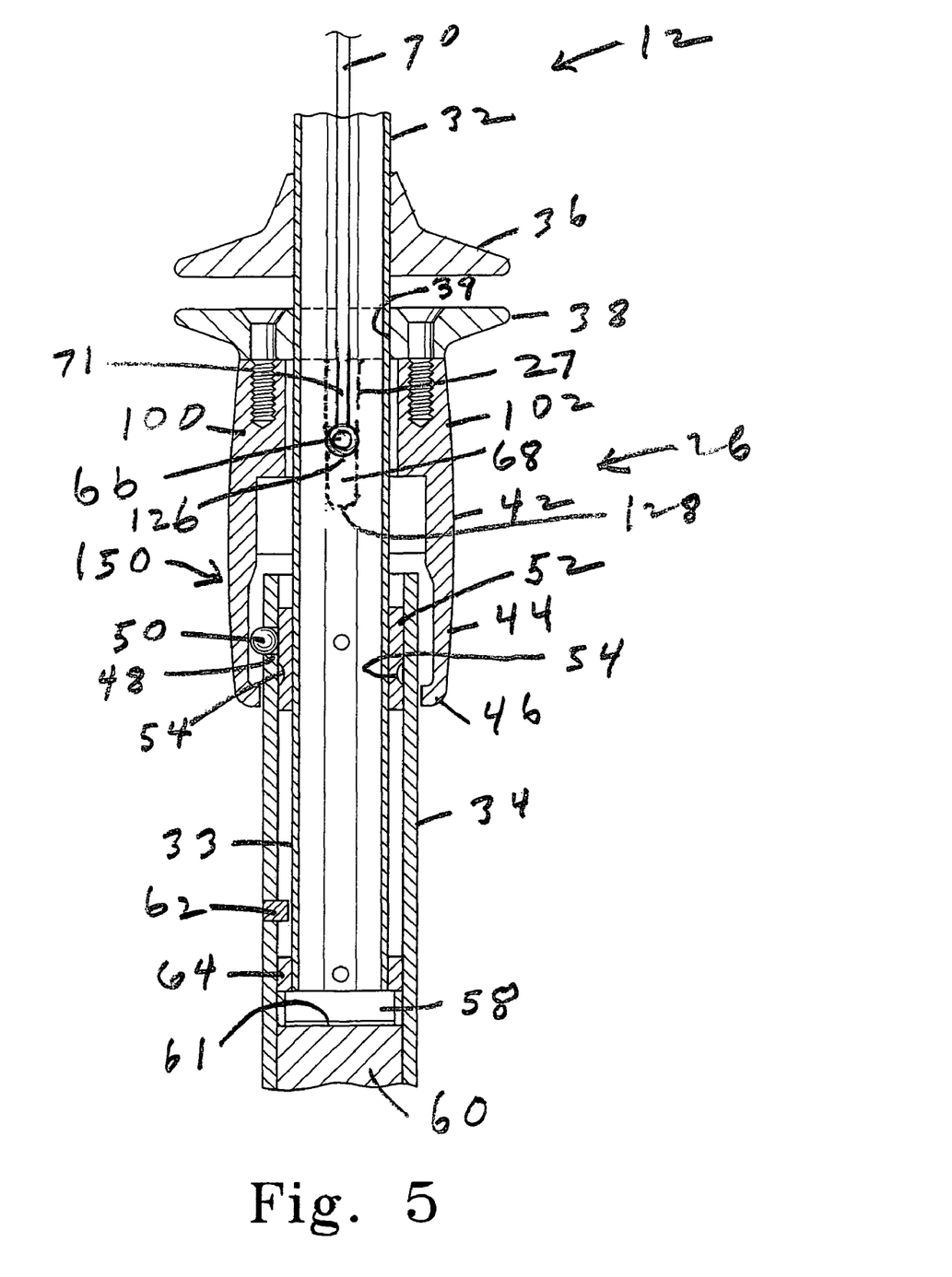
FIG. 5 is a cross-sectional view similar to FIGS. 3 and 4 showing the actuator in a third or upper position.

A fixed handle 36 is coupled to the middle tube 32 by suitable fasteners, such as screws. The fixed handle 36 has a bore 37 through which the middle tube 32 extends as shown in FIGS. 3-5. The post 60 extends downwardly from a lower end 35 of the lower tube 34. The post 60 is configured for receipt in a complementary bore in the socket 16 of the bed 18 when the IV pole is supported by the bed 18. The post 60 has a shallow or slight taper in a downward direction to facilitate engagement between the post 60 and the socket 16. A top surface 61 of the post 60 limits the downward movement of the middle tube 32 relative to the lower tube 32. A spring 58 is disposed between the top surface 61 of the post 60 and the bushing 64 coupled to the lower end of the middle tube 32 as shown in FIGS. 3-5. A stop 62 extends inwardly from the inner surface of the lower tube 34. The spring 58 biases the lower tube 34 to move downwardly relative to the middle tube 32 until the stop 62 engages the bushing 64 as shown in FIG. 3. A horizontal support member 29 is coupled to the upper end of the upper tube 30 as shown in FIG. 2. The support member 29 has hooks 17 for supporting IV bags (not shown)

Figure 10:
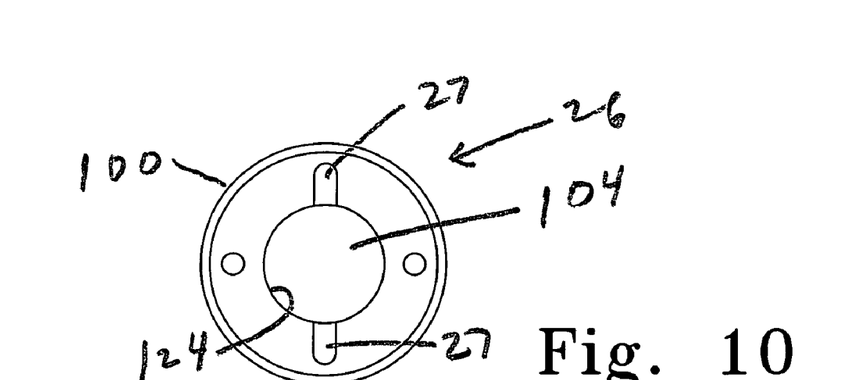
FIG. 10 shows a top view of the actuator.
Figure 11:
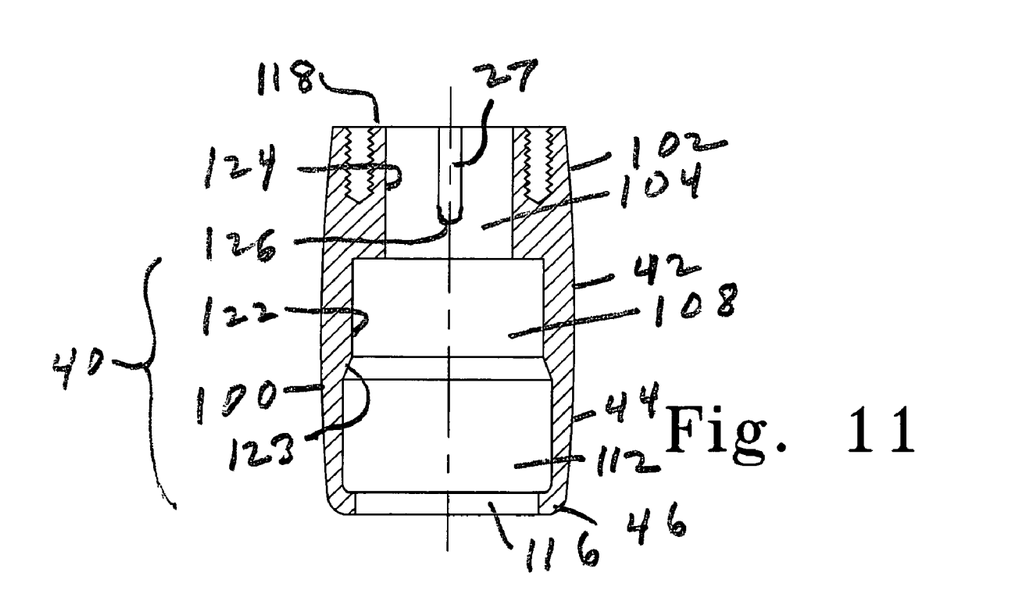
FIG. 11 shows a cross-sectional view of the actuator.

As shown in FIGS. 10 and 11, the actuator 26 has a generally cylindrical-shaped body 100 comprising an upper portion 102 having a small diameter bore 104, a middle portion 42 having an intermediate diameter bore 108, and a lower portion 44 having a large diameter bore 112. The body 100 has a tapered inner surface 123 interconnecting the inner surface of the intermediate diameter bore 108 of the middle portion 42 with the inner surface of the large diameter bore 112 of the lower portion 44. The middle and lower portions 42, 44 collectively form a sleeve portion 40 of the actuator 26. An inwardly-extending rim portion 46, having an intermediate diameter bore 116, is formed at a lower end of the lower portion 44.

As shown in FIGS. 3-5, a top cover 38 is coupled to a top wall 118 of the upper portion 102 of the actuator 26 by suitable fasteners, such as screws. The middle tube 32 is slidingly received for longitudinal movement in a bore 39 in the top cover 38 of the actuator 26. The lower tube 34 is slidingly received for longitudinal movement in the intermediate diameter bores 108, 116 in the middle portion 42 and the rim portion 46, respectively. The caregiver grips the actuator 26 just below the top cover 38 to move the actuator 26 relative to the lower tube 34.

The IV pole 12 includes an upper lock 140 housed in the upper tube 30 and a lower lock 150 housed in the lower tube 34. The upper lock 140 selectively locks the middle tube 32 to the upper tube 30 to prevent relative movement therebetween. The lower lock 150 selectively locks the middle tube 32 to the lower tube 34 to prevent relative movement therebetween. The upper and lower locks 140, 150 are operated by the actuator 26. When the actuator 26 is in the lower position shown in FIG. 3, both the upper and lower locks 140, 150 are locked to prevent relative movement between the upper, middle and lower tubes 30, 32, 34. When the actuator 26 is in the middle position shown in FIG. 4, the upper lock 140 remains locked to prevent relative movement between the upper and middle tubes 30, 32 but the lower lock 150 is released to allow relative movement between the middle and lower tubes 32, 34. When the actuator 26 is in the upper position shown in FIG. 5, both the upper and lower lock 130 are released to allow relative movement between the upper, middle and lower tubes 30, 32, 34.

Figure 6:
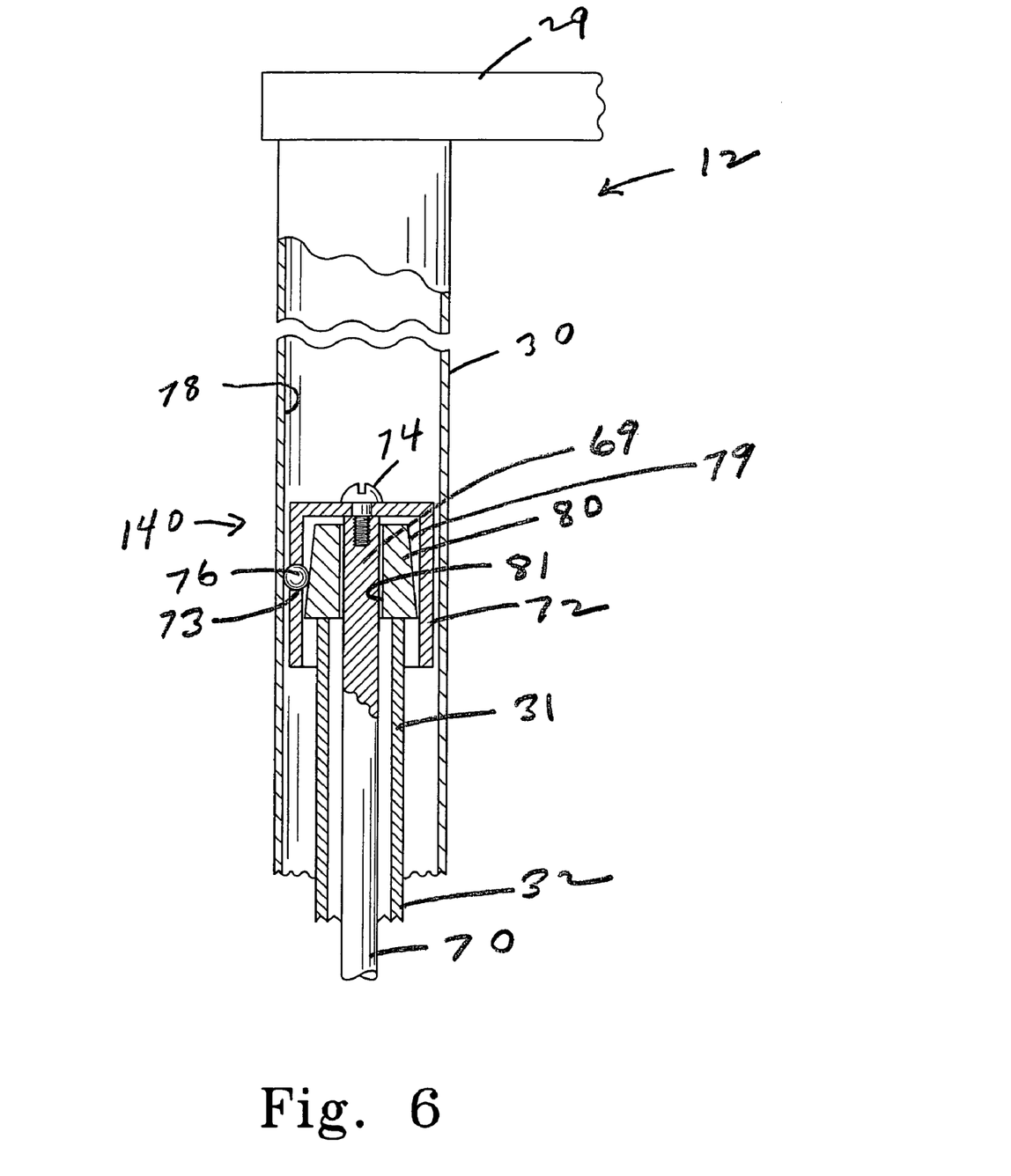
FIG. 6 is a cross-sectional view of the upper portion of the IV pole showing an upper lock and a push rod which, when raised, releases the upper lock.

The construction and operation of the upper lock 140 is as follows. As shown in FIG. 6, a tapered cone 80 is coupled to an upper end 31 of the middle tube 32. A push rod 70 is located inside the middle tube 32 for longitudinal movement therein between a lowered locking position shown in FIG. 6 and a raised unlocking position (not shown). The push rod 70 has an upper end 69 that extends through a bore 81 in the tapered cone 80. An inverted cup 72 is coupled to the upper end 69 of the push rod 70 by a screw 74. The cup 72 sleeves over the tapered cone 80 for axial movement relative thereto.

Three equi-spaced apertures 73 are radially disposed in the cup 72. A ball 76 is positioned within each aperture 73 for radial movement therein relative to the cup 72. The diameter of each ball 76 is larger than the wall thickness of the cup 72 so that portions of the balls 76 project into the interior region of the cup 72. The balls 76 are disposed between the inner surface 78 of the upper tube 30 and the outer surface 79 of the tapered cone 80. When the push rod is in the lowered locking position shown in FIG. 6, the balls 76 are wedged between the inner surface 78 of the upper tube 30 and the outer surface 79 of the tapered cone 80 to lock the upper tube 30 to the middle tube 32. However, when the push rod 70 is raised relative to the middle tube 32, the cup 72 carrying the balls 76 is raised therewith so that the balls 76 are situated at a location in which the spacing between the inner surface 78 of the upper tube 30 and the outer surface 79 of the tapered cone 80 is greater than the diameter of the balls 76 to allow relative movement between the upper and middle tubes 30, 32.

Figure 9:
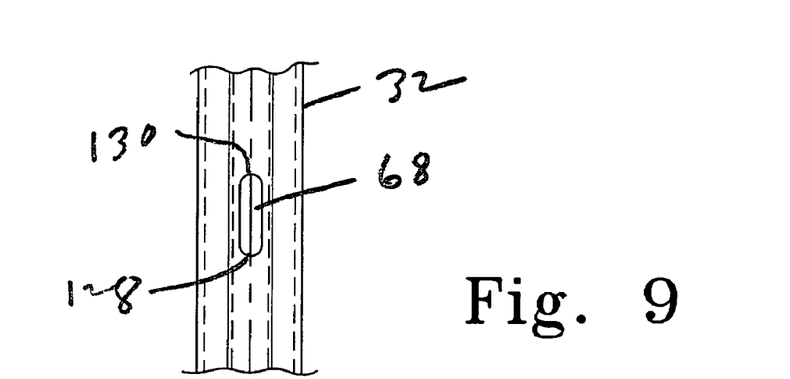
FIG. 9 is a front elevation view of a portion of a middle tube of the IV pole having a pair of oppositely disposed slots therein.

A release pin or tab 66 is coupled to a lower end 71 of the push rod 70 as shown in FIGS. 3-5. The opposite ends of the release pin 66 extend through oppositely-disposed vertical slots 68 (shown best in FIG. 9) in the middle tube 32 and ride in oppositely-disposed vertical grooves 27 (shown best in FIGS. 10, 11) formed in the inner surface 124 of the upper portion 102 of the actuator 26. When the actuator 26 is in the lower position shown in FIG. 3, the opposite ends of the release pin 66 are spaced from bottom portions 126 of the vertical grooves 27 in the actuator 26. When the actuator 26 moves from the lower position shown in FIG. 3 to the middle position shown in FIG. 4, the opposite ends of the release pins 66 engage the bottom portions 126 of the vertical grooves 27 in the actuator 26. When the actuator 26 moves from the middle position shown in FIG. 4 to the upper position shown in FIG. 5, the bottom portions 126 of the vertical grooves 27 in the actuator 26 lift the release pin 66 to, in turn, lift the push rod 70 to the raised position to release the upper lock 140 to allow relative movement between the upper and middle tubes 30, 32.

When the actuator 26 is in the lower position shown in FIG. 3, the opposite ends of the release pin 66 are near the bottom portions 128 (shown in FIG. 9) of the vertical slots 68 in the middle tube 32. When the actuator 26 moves from the lower position shown in FIG. 3 to the middle position shown in FIG. 4, the push rod 70 carrying the release pin 66 does not move relative to the middle tube 32. Therefore, when the actuator 26 moves from the lower position shown in FIG. 3 to the middle position shown in FIG. 4, the opposite ends of the release pin 66 remain near the bottom portions 128 of the vertical slots 68 in the middle tube 32. However, when the actuator 26 moves from the middle position shown in FIG. 4 to the upper position shown in FIG. 5, the push rod 70 carrying the release pin 66 moves therewith relative to the middle tube 32 to the raised position and the opposite ends of the release pin 66 move near the top portions 130 (shown in FIG. 9) of the vertical slots 68 in the middle tube 32. Thus, the bottom and top portions 128, 130 of the vertical slots 68 in the middle tube 32 define the lower and upper limits of the vertical movement of the release pin 66 relative to the middle tube 32.

In summary, when the actuator 26 is in the lower position shown in FIG. 3 and the middle position shown in FIG. 4, the push rod 70 is in the lowered position and the upper lock 150 is locked to prevent relative movement between the upper and middle tubes 30, 32. When the actuator 26 moves to the upper position shown in FIG. 5, the push rod 70 is in the raised position and the upper lock 150 is released to allow relative movement between the upper and middle tubes 30, 32. The actual number of balls 76 in the upper lock 140 depends on design considerations. Accordingly, while the illustrated upper lock 140 has three balls 76, the upper lock 140 may very well have more or less than three balls.

The construction and operation of the lower lock 150 is as follows. Referring to FIGS. 3-5, three equi-spaced apertures 48 are radially disposed in the lower tube 34. A ball 50 is positioned within each aperture 48 for radial movement therein relative to the lower tube 34. The diameter of each ball 50 is larger than the wall thickness of the lower tube 34 so that portions of the balls 50 either project into the interior region of the lower tube 34 as shown in FIG. 3 or project outside the outer surface of the lower tube 34 as shown in FIGS. 4, 5. A circumferential groove 54 for receiving the balls 50 is formed in the upper bushing 52 coupled to the middle tube 32. The spring 58 biases the lower tube 34 to move downwardly relative to the middle tube 32 until the stop 62 coupled to the lower tube 34 engages the lower bushing 64 coupled to the middle tube 32 as shown in FIG. 3. When the stop 62 engages the lower bushing 64, the balls 50 in the apertures 48 are aligned with the circumferential groove 54 in the upper bushing 52.

When the actuator 26 is in the lower position relative to the lower tube 34 as shown in FIG. 3, the balls 50 in the apertures 48 are situated within the smaller diameter middle portion 42 of the actuator 26. When the balls 50 in the apertures 48 are situated within the smaller diameter middle portion 42 and the stop 62 is in engagement with the lower bushing 64, the inner surface 122 (shown in FIG. 11) of the middle portion 42 holds the balls 50 in the circumferential groove 54 in the upper bushing 52 to lock the lower tube 34 to the middle tube 32.

When the actuator 26 is moved in the direction indicated by arrow 56 relative to the lower tube 34 to the middle position shown in FIG. 4 and the upper position shown in FIG. 5, the balls 50 in the apertures 48 are situated within the larger diameter lower portion 44 of the actuator 26. When the balls 50 in the apertures 48 are situated within the larger diameter lower portion 44, the balls 50 are free to move radially outwardly away from the circumferential groove 54 to allow relative movement between the middle and lower tubes 32, 34. Thus, when the actuator 26 is in the lower position shown in FIG. 3, the lower lock 150 is locked to prevent relative movement between the middle and lower tubes 30, 32. When the actuator 26 moves to the middle position shown in FIG. 4 and the upper position shown in FIG. 5, the lower lock 150 is released to allow relative movement between the middle and lower tubes 30, 32. The actual number of balls 50 in the lower lock 150 depends on design considerations. Accordingly, while the illustrated lower lock 150 has three balls 50, the lower lock 150 may very well have more or less than three balls.

In summary, when the actuator 26 is in the lower position shown in FIG. 3, both the upper and lower locks 140, 150 are locked to prevent relative movement between the upper, middle and lower tubes 30, 32, 34. When the actuator 26 is in the middle position shown in FIG. 4, the upper lock 140 remains locked to prevent relative movement between the upper and middle tubes 30, 32 but the lower lock 150 is released to allow relative movement between the middle and lower tubes 32, 34. When the actuator 26 is in the upper position shown in FIG. 5, both the upper and lower lock 130 are released to allow relative movement between the upper, middle and lower tubes 30, 32, 34.

Illustratively, the upper and lower tubes 30, 34 have cylindrical inner and outer surfaces, the middle tube 32 has octagonal inner and outer surfaces, the bushings 52, 64 have octagonal inner surfaces and cylindrical outer surfaces, the bores 104, 108, 112 in the actuator 26 have circular cross sections, and the bore 37 in the fixed handle 36 and the bore 39 in the top cover 38 of the actuator 26 have octagonal cross-sections to complement the octagonal outer surface of the middle tube 32.

In the illustrative embodiment, the IV pole 12 is interchangeably supported by the gripper 20 of the column 14 and the socket 16 of the bed 18 as shown in FIG. 1. To transfer the IV pole 12 from the column 14 to the bed 18, the IV pole 12 is positioned above the socket 16 and the actuator 26 is actuated by moving the actuator 26 from the lower position shown in FIG. 3 to the upper position shown in FIG. 5. Such movement of the actuator 26 to the upper position shown in FIG. 5 unlocks both the upper and lower locks 140, 150. Unlocking of the upper lock 140 permits the middle tube 34 to telescope downwardly out of the lower end of the upper tube 30 until the downwardly-extending tapered post 60 of the lower tube 34 engages the socket 16 of the bed 18.

Figure 7:
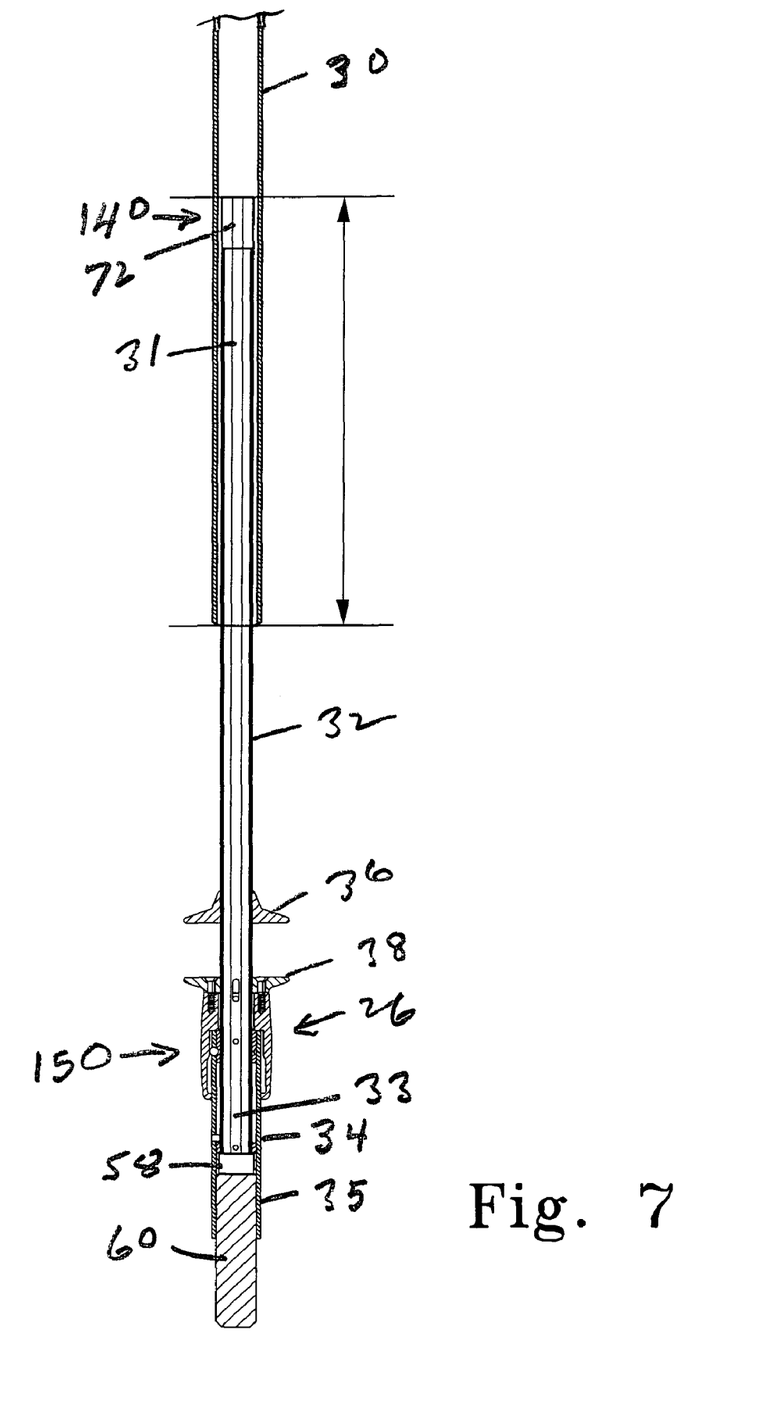
FIG. 7 is a cross-sectional view of the IV pole in a partially extended position.

As the middle tube 32 telescopes out of the lower end of the upper tube 30, the spring 58 keeps the balls 50 in the apertures 48 in the lower tube 34 aligned with the circumferential groove 54 in the upper bushing 52 coupled to the middle tube 32 as shown in FIG. 3. Upon engagement of the post 60 with the socket 16, the actuator 26 is released so that the actuator 26 and the push rod 70 resume their respective lower positions as shown in FIGS. 3 and 6, respectively. As the actuator 26 moves to its lower position, the tapered inner surface 123 of the actuator 26 drives the balls 50 of the lower lock 150 into the circumferential groove 54 in the upper bushing 52 coupled to the middle tube 32 to lock the lower tube 34 to the middle tube 32 as shown in FIG. 3. As the push rod 70 moves to its lower position, the balls 76 of the upper lock 140 are wedged between the inner surface 78 of the upper tube 30 and the outer surface 79 of the tapered cone 80 coupled to the middle tube 32 to lock the middle tube 32 to the upper tube 30 as shown in FIG. 6. The relative positions of the upper, middle and lower tubes 30, 32, 34 when the IV pole 12 is in the partially extended position are shown in FIG. 7.

The gripper 20 of the column 14 is thereafter released from engagement with upper tube 30, and the column 14 is moved away from the IV pole 12 and the bed 18. As the gripper 20 is released, the weight of the IV pole 12, along with the weight of the IV bags, if any, (hereinafter the "load of the IV pole 12") is transferred from the upper tube 30 of the IV pole to the middle tube 32 through the upper lock 140, from the middle tube 32 to the lower tube 34 through the lower lock 150, and then from the lower tube 34 to the socket 16 of the bed 18 through the post 60.

To transfer the IV pole 12 from the bed 18 to the column 14, the column 14 is moved to a position near the bed 18 and the gripper 20 is coupled to the upper tube 30 of the IV pole 12. At this time, although the gripper 20 is coupled to the IV pole 12, the load of the IV pole 12 is still supported by the bed 18. The actuator 26 is thereafter actuated by moving the actuator 26 from the lower position shown in FIG. 3 to the upper position shown in FIG. 5 through the middle position shown in FIG. 4. Initial movement of the actuator 26 from the lower position shown in FIG. 3 to the middle position shown in FIG. 4 unlocks the lower lock 150. When the lower lock 150 is unlocked, the load of the IV pole 12 causes the middle tube 34 to telescope downwardly into the lower tube 34, thereby compressing the spring 58 as shown in FIG. 4. Downward movement of the middle tube 32 into the lower tube 34, allows the radial arm 15 or other structure supporting the column 14 to flex downwardly therewith by a slight amount, thereby transferring the load of the IV pole 12 from the bed 18 to the column 14 and releasing the pressure on the upper and lower locks 140, 150.

As the actuator 26 moves from the middle position shown in FIG. 4 to the upper position shown in FIG. 5, the release pin 66 lifts the push rod 70 to unlock the upper lock 140 to allow the caregiver to telescope the middle tube 132 upwardly relative to the upper tube 30. As the middle tube 32 is retracted upwardly into the upper tube 30, the post 60 is lifted out of the socket 16 and the spring 58 causes the lower tube 34 to return to its initial position shown in FIG. 3 where the balls 50 in the apertures 48 in the lower tube 34 are aligned with the circumferential groove 54 in the upper bushing 52 coupled to the middle tube 32.

Figure 8:
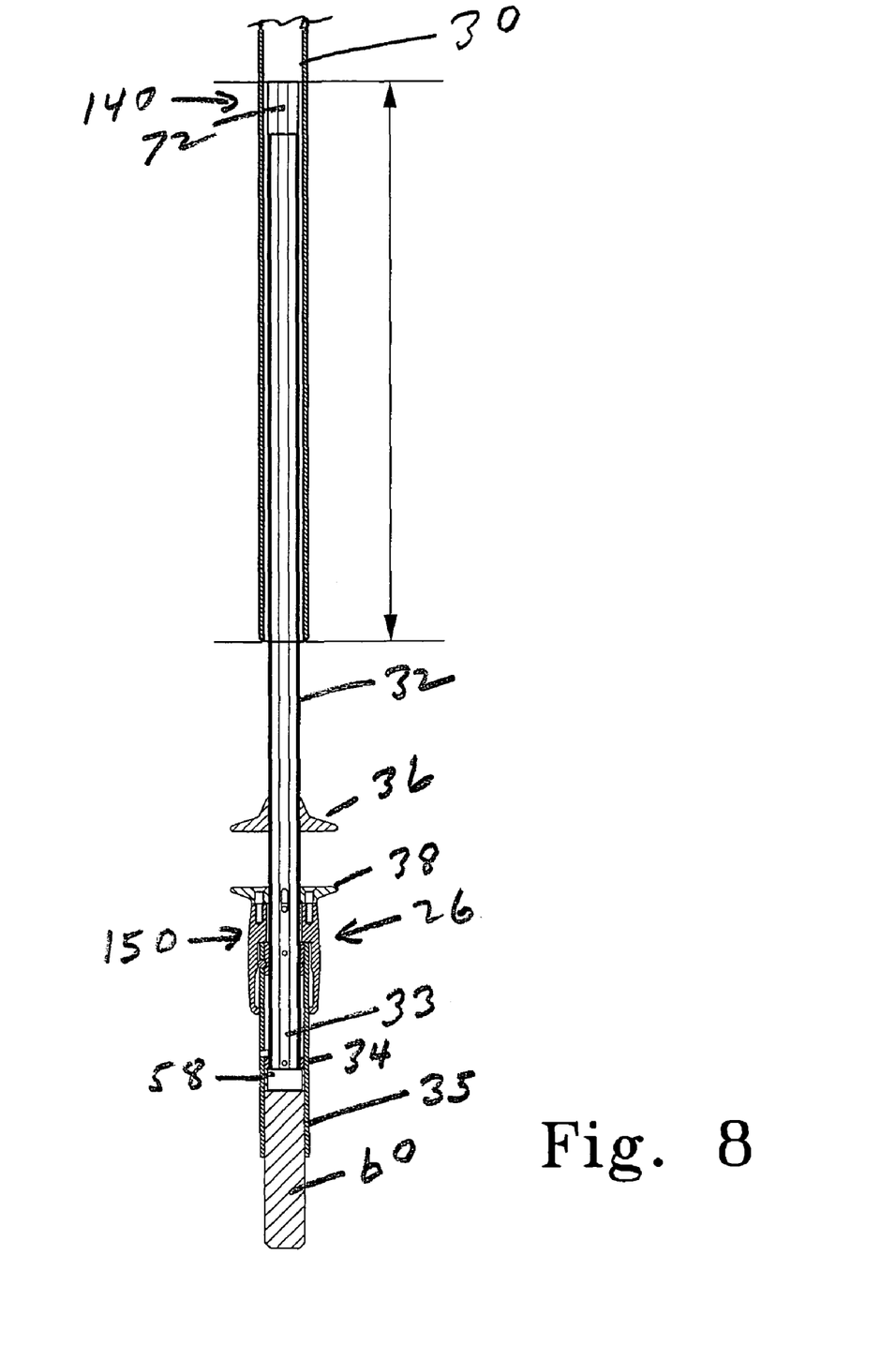
FIG. 8 is a cross-sectional view of the IV pole in a partially retracted position.

Upon retraction of the middle tube 32 upwardly into the upper tube 30, the actuator 26 is released so that the actuator 26 and the push rod 70 resume their respective lower positions shown in FIGS. 3 and 6, respectively. As the actuator 26 moves to its lower position, the tapered inner surface 123 of the actuator 26 drives the balls 50 of the lower lock 150 into the circumferential groove 54 in the upper bushing 52 coupled to the middle tube 32 to lock the lower tube 34 to the middle tube 32 as shown in FIG. 3. As the push rod 70 moves to its lower position, the balls 76 of the upper lock 140 are wedged between the inner surface 78 of the upper tube 30 and the outer surface 79 of the tapered cone 80 coupled to the middle tube 32 to lock the middle tube 32 to the upper tube 30 as shown in FIG. 6. The relative positions of the upper, middle and lower tubes 30, 32, 34 when the IV pole 12 is in the partially retracted position are shown in FIG. 8.

Without the releasable lower lock 150, it may be difficult to manually retract the middle tube 32 into the upper tube 30 after the gripper 20 of the column 14 is coupled to the IV pole 12 due the load of the IV pole 12 bearing down on the upper lock 140. Under these circumstances, either the upper frame 19 of the bed 18 carrying the socket 16 would have to be lowered or, in the alternative, the column 14 carrying the gripper 20 would have to be raised to transfer the load of the IV pole 12 from the bed 18 to the column 14, thereby releasing the pressure on the upper lock 150 and allowing the caregiver to telescope the middle tube 132 back into the upper tube 30. A motorized drive may be required to lower the upper frame 19 of the bed 18 or to raise the column 14. Providing the IV pole 12 with the releasable lower lock 150 allows transfer of the load of the IV pole 12 from the bed 18 to the column 14, thereby releasing the pressure on the upper lock 150 and allowing the caregiver to manually telescope the middle tube 132 back into the upper tube 30 without the need for a motorized drive.

While the disclosure is susceptible to various modifications and alternative forms, specific exemplary embodiments thereof have been shown by way of example in the drawings and have herein been described in detail. It should be understood, however, that there is no intent to limit the disclosure to the particular forms disclosed, but on the contrary, the intention is to cover all modifications, equivalents, and alternatives falling within the spirit and scope of the disclosure as defined by the appended claims.

There is a plurality of advantages of the present invention arising from the various features of the embodiments described herein. It will be noted that alternative embodiments of the present invention may not include all of the features described yet still benefit from at least some of the advantages of such features. Those of ordinary skill in the art may readily devise their own implementations of a device that incorporates one or more of the features of the present invention and fall within the spirit and scope of the present invention as defined by the appended claims.

The invention claimed is:

1. A patient care equipment support comprising:
   an upper portion,
   a lower portion having a lower end configured to engage a socket, the lower portion telescoping relative to the upper portion, and the lower end telescoping relative to the lower portion, and
   an actuator non-rotationally coupled to the lower portion for movement between functionally distinct first, second, and third positions.

2. The equipment support of claim 1, wherein the actuator is movable to the first position to block the lower portion from telescoping relative to the upper portion and block the lower end from telescoping relative to the lower portion.

3. The equipment support of claim 1, wherein the actuator is movable to the second position to block the lower portion from telescoping relative to the upper portion but allow the lower end to telescope relative to the lower portion.

4. The equipment support of claim 1, wherein the actuator is movable to the third position to allow the lower portion to telescope relative to the upper portion and allow the lower end to telescope relative to the lower portion.

5. The equipment support of claim 1, further comprising a lower lock operably coupled to the actuator, wherein the actuator is movable to the first position to enable the lower lock to block the telescoping movement of the lower end relative to the lower portion and the actuator is movable to the second position to disable the lower lock to allow telescoping movement of the lower end relative to the lower portion.

6. The equipment support of claim 5, wherein the lower lock includes a radially-disposed aperture in the lower end, a ball disposed in the radially-disposed aperture for radial movement therein, and a collar coupled to the lower portion and having a circumferential groove, a portion of the ball enters the circumferential groove to block the telescoping movement of the lower end relative to the lower portion when the actuator is moved to the first position and the portion of the ball withdraws from the circumferential groove to allow telescoping movement of the lower end relative to the lower portion when the actuator is moved to the second position.

7. The equipment support of claim 5, further comprising an upper lock operably coupled to the actuator, wherein the upper lock is enabled when the actuator is moved to the first position or to the second position to block the telescoping movement of the lower portion relative to the upper portion, and the upper lock is disabled when the actuator is moved to the third position to allow telescoping movement of the lower portion relative to the upper portion.

8. A patient care equipment support comprising:
   an upper portion,
   a lower portion having a lower end configured to engage a socket,
   a movable actuator movable relative to the lower end,
   a lower lock operably coupled to the actuator, wherein the actuator is movable to a first position to enable the lower lock to block the telescoping movement of the lower end relative to the lower portion and the actuator is movable to a second position to disable the lower lock to allow telescoping movement of the lower end relative to the lower portion, and
   an upper lock operably coupled to the actuator, wherein the upper lock is enabled when the actuator is moved to the first position or to the second position to block the telescoping movement of the lower portion relative to the upper portion, and the upper lock is disabled when the actuator is moved to a third position to allow telescoping movement of the lower portion relative to the upper portion, wherein the upper lock includes a tab, the lower portion includes a vertically-disposed slot for receiving the tab, the tab is vertically movable within the slot, the tab is near a bottom end of the slot when the actuator is in the first position or the second position, and the tab moves to a top end of the slot when the actuator is moved to a third position to allow the lower portion to telescope relative to the upper portion.

9. The equipment support of claim 1, for use in transferring the equipment support between a socket on a patient support and a releasable gripper on a piece of equipment, wherein a lower portion of the lower end is configured for reception in the socket to allow the patient support to carry the equipment support, and the upper portion is configured to be releasably gripped by the releasable gripper to allow the piece of equipment to carry the equipment support.

10. The equipment support of claim 1, wherein, when the upper portion is gripped by a releasable gripper, the lower end can be disengaged from a socket after moving the actuator from the first position to the second position.

11. The equipment support of claim 10, wherein the lower portion can be telescoped relative to the upper portion after moving the actuator from the second position to the third position.

12. The equipment support of claim 10, wherein the weight of the actuator biases the actuator to return to the first position thereof.

13. The equipment support of claim 1, further comprising a spring to urge the lower end downwardly from the lower portion.

14. A patient care equipment support comprising:
   an upper portion,
   a lower portion having a lower end configured to engage a socket, and
   an actuator non-rotationally coupled to the lower portion for movement between functionally distinct first, second, and third positions, wherein, when the upper portion is gripped by a releasable gripper, the lower end can be disengaged from a socket after moving the actuator from a first position to a second position.

15. The equipment support of claim 14, wherein the lower portion can be telescoped relative to the upper portion after moving the actuator from the second position to the third position.

16. A patient care equipment support comprising:
   an equipment supporting portion configured to support patient care equipment, and
   a downwardly-extending portion coupled to the equipment supporting portion, the downwardly-extending portion comprising:
   an upper tube,
   a middle tube telescoping relative to the upper tube,
   a lower tube telescoping relative to the middle tube,
   an upper lock to selectively lock the middle tube to the upper tube,
   a lower lock to selectively lock the lower tube to the middle tube, and
   an actuator operably coupled to the upper and lower locks, wherein the actuator is movable to a first position to enable both the upper and lower locks to block telescoping movement of the middle tube relative to the upper tube and block telescoping movement of the lower tube relative to the middle tube, the actuator is movable to a second position to disable the lower lock to allow telescoping movement of the lower tube relative to the middle tube, and the actuator is movable to a third position to disable both the upper and lower locks to allow telescoping movement of the middle tube relative to the upper tube and allow telescoping movement of the lower tube relative to the middle tube.

17. The patient support of claim 16, further comprising a spring to urge the lower tube downwardly from the middle tube.

18. A patient care equipment support comprising:
an equipment supporting portion configured to support patient care equipment, and
a downwardly-extending portion coupled to the equipment supporting portion, the downwardly-extending portion comprising:
an upper tube,
a middle tube telescoping relative to the upper tube,
a lower tube telescoping relative to the middle tube, and
an actuator non-rotationally coupled to the middle tube, the actuator being movable to a first position to block the middle tube from telescoping relative to the upper tube and block the lower tube from telescoping relative to the middle tube, the actuator being movable to a second position to continue to block the middle tube from telescoping relative to the upper tube but allow the lower tube to telescope relative to the middle tube, the actuator being movable to a third position to allow the middle tube to telescope relative to the upper tube and allow the lower tube to telescope relative to the lower tube.

19. A patient care equipment support comprising:
an upper portion,
a lower portion having a lower end configured to engage a socket, the lower portion telescoping relative to the upper portion, and the lower end telescoping relative to the lower portion, and
an actuator moveable with respect to the upper portion, the lower portion and the lower end and non-rotationally coupled to the lower portion for movement between first, second, and third positions.

\* \* \* \* \*